(12) United States Patent
Zheng et al.

(10) Patent No.: US 7,750,106 B2
(45) Date of Patent: Jul. 6, 2010

(54) COSMETIC COMPOSITIONS HAVING IN-SITU HYDROSILYLATION CROSS-LINKING

(75) Inventors: Tao Zheng, Nanuet, NY (US); Derrick B. McKie, Brooklyn, NY (US); John C. Brahms, Morris Plains, NY (US); Prithwiraj Maitra, Morristown, NJ (US)

(73) Assignee: Avon Products, Inc., New York, NY (US)

( * ) Notice: Subject to any disclaimer, the term of this patent is extended or adjusted under 35 U.S.C. 154(b) by 425 days.

(21) Appl. No.: 11/314,393

(22) Filed: Dec. 21, 2005

(65) Prior Publication Data
US 2007/0142575 A1    Jun. 21, 2007

(51) Int. Cl.
C08G 77/04    (2006.01)
(52) U.S. Cl. ............... 528/34; 528/15; 528/19
(58) Field of Classification Search ............ 528/15, 528/19, 34
See application file for complete search history.

(56) References Cited

U.S. PATENT DOCUMENTS

| | | | |
|---|---|---|---|
| 3,159,601 A | 12/1964 | Ashby | |
| 3,159,662 A | 12/1964 | Ashby | |
| 3,220,972 A | 11/1965 | Lamoreaux | |
| 3,445,420 A | 5/1969 | Kookootsedes et al. | |
| 3,715,334 A | 2/1973 | Karstedt | |
| 3,757,782 A | 9/1973 | Aiken | |
| 3,775,452 A | 11/1973 | Karstedt | |
| 3,814,730 A | 6/1974 | Karstedt | |
| 4,196,808 A | 4/1980 | Pardo | |
| 4,202,879 A | 5/1980 | Shelton | |
| 4,256,870 A | 3/1981 | Eckberg | |
| 4,465,818 A | 8/1984 | Shirahata et al. | |
| 4,562,096 A | 12/1985 | Lo et al. | |
| 4,578,266 A | 3/1986 | Tietjen et al. | |
| 4,681,963 A | 7/1987 | Lewis | |
| 4,699,780 A | 10/1987 | Jennings et al. | |
| 4,781,917 A | 11/1988 | Luebbe et al. | |
| 4,816,261 A | 3/1989 | Luebbe et al. | |
| 4,832,944 A | 5/1989 | Socci et al. | |
| 4,935,228 A | 6/1990 | Finkenaur et al. | |
| D326,606 S | 6/1992 | Green | |
| 5,225,195 A | 7/1993 | Soyama et al. | |
| 5,318,203 A | 6/1994 | Iaia et al. | |
| 5,318,775 A | 6/1994 | Shore et al. | |
| 5,340,569 A | 8/1994 | Elliott et al. | |
| 5,424,061 A | 6/1995 | Pappas et al. | |
| 5,482,547 A | 1/1996 | Bugnon et al. | |
| 5,543,443 A * | 8/1996 | Rajaiah et al. ............ 523/120 |
| 5,607,665 A | 3/1997 | Calello et al. | |
| 5,629,387 A | 5/1997 | Frances et al. | |
| 5,688,831 A | 11/1997 | El-Nokaly et al. | |
| 5,747,017 A | 5/1998 | Nichols et al. | |
| 5,789,334 A | 8/1998 | Nakanishi et al. | |
| 5,863,523 A | 1/1999 | Socci et al. | |
| 5,977,217 A | 11/1999 | Socci et al. | |
| 6,074,654 A | 6/2000 | Drechsler et al. | |
| 6,126,952 A | 10/2000 | Socci et al. | |
| 6,247,586 B1 | 6/2001 | Herzog et al. | |
| 6,261,576 B1 | 7/2001 | Fishman | |
| 6,290,935 B1 | 9/2001 | Masters et al. | |
| D449,224 S | 10/2001 | Kaufman | |
| 6,303,728 B1 | 10/2001 | Hagimori et al. | |
| 6,307,082 B1 | 10/2001 | Klein et al. | |
| 6,428,797 B2 | 8/2002 | Fishman | |
| 6,471,950 B1 | 10/2002 | Farer et al. | |
| 6,509,009 B2 | 1/2003 | Nichols et al. | |
| 6,512,072 B1 | 1/2003 | Gantner et al. | |
| 6,514,483 B2 | 2/2003 | Xu et al. | |
| 6,770,266 B2 | 8/2004 | Santarpia, III et al. | |
| 6,780,402 B1 | 8/2004 | Agostini et al. | |
| 6,789,971 B2 | 9/2004 | Tsaur | |
| 6,824,704 B2 | 11/2004 | Chadwick et al. | |
| 2004/0110112 A1 * | 6/2004 | Xie et al. ............ 433/89 |
| 2004/0165935 A1 | 8/2004 | Kauffmann et al. | |
| 2005/0000531 A1 | 1/2005 | Shi | |

FOREIGN PATENT DOCUMENTS

| | | | |
|---|---|---|---|
| EP | 90311291.0 | | 10/1990 |
| EP | 865 787 | * | 9/1998 |

OTHER PUBLICATIONS

Speier, J.L. et al., "The Addition of Silicon Hydrides to Olefinic Double Bonds", J. Amer. Chem. Soc., vol. 79, 974 (1957).
Lewis, L.N. and N. Lewis, "Platinum-Catalysed Hydrosilylation-Colloid Formation as the Essential Step", J. Am. Chem. Soc. vol. 108, 7228 (1986).
Jens Uhlemann et al., "Flavor Encapsulation Technologies: An Overview Including Recent Developments", Perfumer and Flavorist, Vo. 27, 52-61 (2002).
R. Sparks and I. Jacobs, "Selection of Coating and Microencapsulation Processes", Controlled-Release Delivery Systems for Pesticides, Herbert B. Scher ed., 3-29, (1999).
Cosmestic, Science, and Technology, vol. 1, 27-104 edited by Balsam and Sagarin (1972).
C. Todd and T. Byers, "Volatile Silicone Fluids for Cosmetics", Cosmetics and Toiletries, vol. 91 27-32 (1976).

* cited by examiner

Primary Examiner—Kuo-Liang Peng
(74) Attorney, Agent, or Firm—Joan M. McGillycuddy; Charles J. Zeller; Anthony M. Santini

(57) ABSTRACT

Compositions and methods for the in situ formation of hydrosilylation (addition) cross-linked organosiloxane films are disclosed. The disclosed films are long-lasting, flexible, transfer-resistant, and water-proof. The film-forming compositions generally comprise alkoxy-terminated organosiloxane polymers and a catalyst and are useful for formulating cosmetics and personal care products.

10 Claims, No Drawings

COSMETIC COMPOSITIONS HAVING IN-SITU HYDROSILYLATION CROSS-LINKING

FIELD OF INVENTION

The present invention relates generally to compositions and methods for forming films on a surface. More particularly, the invention relates to films formed by in situ hydrosilylation (addition) cross-linking of organosiloxane polymers.

BACKGROUND OF THE INVENTION

Many cosmetics and personal care products employ various film forming agents to aid in spreading and adhering a formulation to a surface such as skin. The class of polymers known as organosiloxanes, including polydimethylsiloxane (PDMS or Dimethicone), have recently received considerable attention as film-formers in cosmetic products due to their excellent spreading properties and biological inertness. Examples of cosmetic formulations including organosiloxane film formers include, for example, U.S. Pat. No. 6,780,402 (L'Oreal), U.S. Pat. No. 5,318,775 (Mary Kay Cosmetics), U.S. Pat. No. 4,699,780 (Estee Lauder); and U.S. Pat. No. 4,578,266 (Revlon), the disclosures of which are hereby incorporated by reference. In the case of the foregoing patents, the organosiloxane polymers do not undergo cross-linking to form more robust films when applied to a surface and therefore are of limited durability, transfer resistance, and water-resistance.

Recently, in situ condensation cross-linking organsiloxane film formation has been described in U.S. Pat. No. 6,512,072, the contents of which is hereby incorporated by reference. The described film-forming compositions comprise 5 to 79.9 weight % of an alkylene trialkoxy terminated polysiloxane; 0.01 to 5 weight % of a catalyst; 20 to 94.99 to weight % of a volatile diluent, and, optionally, 0.01 to 5 weight % of an alkoxysilane and 0.1 to 25 weight % of a filler.

In addition to condensation cross-linking, it is known to form cross-linked silicones through the metal-catalyzed addition reaction between olefins and siloxanes having reactive Si—H functionalities. See generally, Speier, J. L. et al., *J. Amer. Chem. Soc.*, 79, 974 (1957); Lewis, L. N.; Lewis N., *J. Am. Chem. Soc.* 108, 7228 (1986), the disclosures of which are hereby incorporated by reference. EP 0465744, which is hereby incorporated by reference, discloses in situ addition reaction cross-linking of a polysiloxane having alkylhydrogen siloxane units with a polysiloxane having unsaturated groups in the presence of a platinum or rhodium catalyst for forming a dressing capable of sustained release of therapeutic or diagnostic agents to the body. EP 0465744

Despite the advances in film forming methods and compositions, there remains a need in the art for in situ cross-linked organosiloxane film formers which provide long-lasting, comfortable, highly flexible, tack-free, and water-proof films.

It is therefore an object of the invention to provide compositions and methods for forming in situ cross-linked organosiloxane films.

It is further an object of the invention to provide cosmetic and personal care compositions comprising in situ cross-linked organosiloxane films.

SUMMARY OF INVENTION

In accordance with the foregoing objectives and others, the present invention overcomes the deficiencies associated with the prior art by providing elastomeric films for use in cosmetics which are highly flexible yet durable and provide a heretofore unobtainable level of comfort to the user.

In one aspect of the invention, a method for forming an elastomeric film on a biological surface is provided. Generally, the method comprises contacting a biological surface, such as skin, nail, hair, and the like, with a siloxane polymer and a hydrosilane in the presence of a cross-linking catalyst. The siloxane polymer will have at least two alkenyl-functionalized terminal groups or alkenyl-functionalized side chains and the hydrosilane polymer will have at least two Si—H units. The cross-linking catalyst induces in situ cross-linking of the siloxane polymer through the addition reaction of the hydrosilane to the terminal groups or side chains to provide a highly elastomeric, water-resistant, oil-resistant and durable (i.e., longwearing) film thereon.

In another aspect of the invention, a method for entrapping a functional agent within an elastomeric film disposed on a biological surface is provided. The method generally comprises contacting the biological surface with a functional agent, a siloxane polymer and a hydrosilane, in the presence of a cross-linking catalyst. The siloxane polymer will have at least two alkenyl-functionalized terminal groups or alkenyl-functionalized side chains and the hydrosilane polymer will have at least two Si—H units. The cross-linking catalyst induces in situ cross-linking of the siloxane polymer through the addition reaction of the hydrosilane to the alkenyl-functionalized terminal groups or side chains to provide a highly elastomeric, water-resistant, oil-resistant and durable film thereon. The film serves to prevent migration or transfer of the active agent by either entrapping the agent within the polymeric network or forming an adhesive film over the active agent which holds it against the surface.

In a further aspect of the invention, formulations for providing an elastomeric film on a biological surface are provided. The formulations generally comprise (i) a first component comprising a siloxane polymer having at least two alkenyl-functionalized terminal groups or alkenyl-functionalized side chains and a cross-linking catalyst, and (ii) a second component comprising a hydrosilane having at least two Si—H units. The first and second components are prevented from coming into intimate contact, together with the catalyst, prior to use. In use, the cross-linking catalyst induces in situ cross-linking of the siloxane polymer through the addition reaction of the hydrosilane to the alkenyl-functionalized terminal groups or side chains of the siloxane polymer to provide a highly elastomeric, water-resistant, oil-resistant and durable film thereon.

These and other aspects of the present invention will become apparent to those skilled in the art after a reading of the following detailed description of the invention, including the illustrative embodiments and examples.

DETAILED DESCRIPTION

The present invention is founded on the discovery that certain cross-linked siloxane polymers are capable of providing flexible cosmetic films on biological surfaces which are long wearing, transfer resistant, waterproof, tack-free, and comfortable to the wearer. The films are formed in situ on the biological surface upon application thereto, meaning that the cross-linking reaction occurs on the surface after application of the film. As used herein, the term "biological surface" is meant to include any surface to which cosmetic and personal care products are applied, including without limitation skin, lips, keratin fibers (eyelashes, eyebrows, or hair), and nails.

a. Film Forming Compositions

An essential component of the invention is a siloxane polymer which is capable of undergoing an addition reaction with a hydrosilane in the presence of a catalyst. The siloxane polymer will have at least two alkenyl-functionalized terminal groups or alkenyl-functionalized side chains and the hydrosilane will have at least two Si—H units.

In the broadest sense of the invention, the selection of siloxane polymer is not particularly limited. However, the polymer will include at least two side chains or terminal groups comprising an alkenyl functional group. In the presence of hydrosilane, the alkenyl-functionalized siloxane polymer undergoes metal catalyzed in situ cross-linking through the addition reaction of hydrosilane with the olefinic moieties. The addition reaction is illustrated below in the non-limiting case of a divinyl-terminated polydimethylsiloxane and a dihydrido-terminated polydimethylsiloxane:

ing without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pentyl; cycloalkyl, heterocycloalkyl, haloalkyl, benzyl, alkyl-aryl; substituted or unsubstituted aryl or heteroaryl groups; $C_1$-$C_6$ alkoxy, amino, alkyl amino, dialkyl amino, hydroxyl, hydrogen, carboxy, cyano, or halogen; or $R_1$, $R_2$, $R_3$, $R_4$, $R_5$, and $R_6$ may each independently represent branching points in the organopolysiloxane backbone whereby D, T, or Q structures are introduced.

In one embodiment, $R_5$, and $R_6$ are both methyl such that the polymer comprises the repeat unit of a polydimethylsiloxane (PDMS) polymer. In another embodiment, $R_1$, $R_2$, $R_3$,

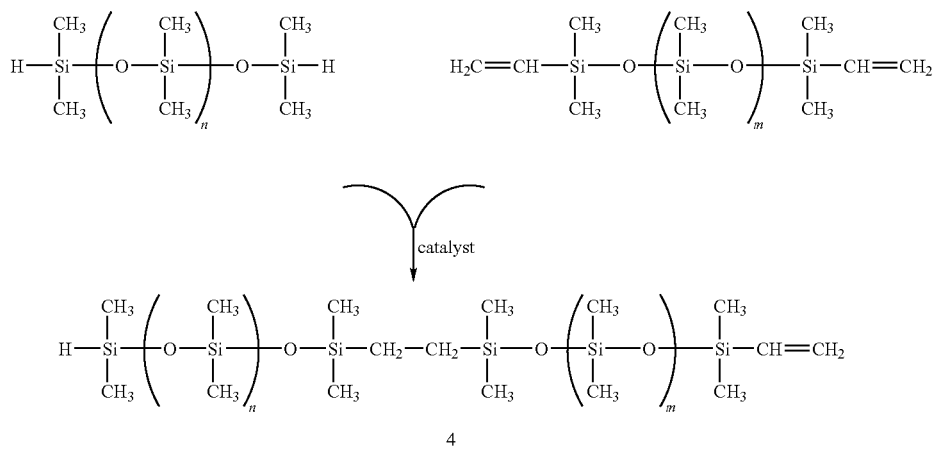

As illustrated above, the addition reaction results in the formation of a Si—C bonds between the hydrosilane and the alkenyl-functionalized siloxane polymer. Because each of the polymers are di-functional, the cross-linking proceeds through further reaction at the hydrosilyl or alkenyl reactive ends of the resultant polymer to create higher order structures.

A necessary component of the invention is alkenyl-functionalized organopolysiloxane. There is essentially no constraint on the selection of a suitable alkenyl-functionalized organopolysiloxane. In certain preferred embodiments, the polymer will comprise at least two alkenyl-functionalized sites which may be at the terminal end of the polymer or on a side chain. The alkenyl functionality is preferably a mono-substituted olefin such as vinyl, 1-propenyl, 1-butenyl, and the like, but may, alternatively by a di-, tri-, or tetra-substituted olefin.

Typically, but not necessarily, the alkenyl-functionalized organopolysiloxanes will have the structure shown in formula I:

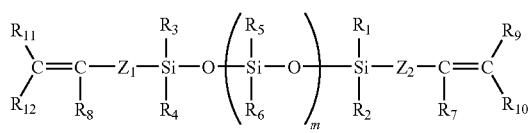

I wherein $R_1$, $R_2$, $R_3$, $R_4$, $R_5$, and $R_6$ are independently selected from substituted or unsubstituted branched or straight chain $C_1$-$C_{10}$ alkyl, alkenyl, or alkynyl group, includand $R_4$ are each methyl. In a preferred embodiment, $R_1$, $R_2$, $R_3$, $R_4$, $R_5$, and $R_6$ are each methyl.

$Z_1$ and $Z_2$ may each represent a bond between Si and the adjacent olefinic carbon atom or $Z_1$ and $Z_2$ may each be a linker moiety independently selected from O; S; $NR^a$ where "$R^a$" represents an alkyl, alkynyl, alkynyl, aryl, heteroaryl, or alkyl-aryl group; substituted or unsubstituted branched or straight chain $C_1$-$C_{10}$ alkyl, alkenyl, alkynyl, aryl, heteroaryl, or alkyl-aryl groups, including without limitation, linear alkyl moieties of the form —$(CH_2)_a$— where "a" is an integer from 1 to 10, including, for example, —$CH_2$—, —$CH_2CH_2$—, —$CH_2CH_2CH_2$—, or —$CH_2CH_2CH_2CH_2$—; linear alkoxy moieties of the general form —$(CH_2)_aO$— or —$O(CH_2)_a$— where "a" is an integer from 1 to 10, including for example, —$CH_2O$— or —$OCH_2$—, —$CH_2CH_2O$— or —$OCH_2CH_2$—, —$CH_2CH_2CH_2O$— or —$OCH_2CH_2CH_2$—; —$O(CH_2)_aO$— where "a" is as defined above; or a moiety of the form —$(CH_2)_bO(CH_2)_c$—, —$(CH_2)_b S(CH_2)_c$—, or —$(CH_2)_b NR^a(CH_2)_c$— wherein "b" and "c" are independently an integer from 0 (zero) to 10 and $R^a$ is as defined above. In preferred embodiments, $Z_1$ and $Z_2$ will comprise an oxygen atom bound to the adjacent Si atom and are therefore exemplified by radicals such as O, —$CH_2O$— or —$OCH_2$—. $Z_1$ may alternatively comprise a non-aromatic ring system together with $R_{11}$, $R_{12}$, or $R_8$ and $Z_2$ may alternatively comprise a non-aromatic ring system together with $R_7$, $R_9$, or $R_{10}$.

$R_7$ and $R_8$ are independently selected from hydrogen or unsubstituted branched or straight chain $C_1$-$C_{10}$ alkyl, alkenyl, or alkynyl group, including without limitation methyl, ethyl, propyl, isopropyl, butyl, isobutyl, t-butyl, n-pentyl, iso-pentyl, neo-pentyl, tert-pentyl, hexyl, vinyl, allyl, butenyl, pentenyl, hexenyl, propynyl, butynyl, pentynyl; cycloalkyl, heterocycloalkyl, haloalkyl, benzyl, alkyl-aryl; substituted or unsubstituted aryl or heteroaryl groups; amino, alkyl amino, dialkyl amino, hydroxyl, hydrido, carboxy, cyano, or halogen. Preferably $R_2$ and $R_3$ are both hydrogen. $R_7$ may alternatively comprise a non-aromatic ring system together with $R_{11}$, $R_{12}$, or $Z_1$.

$R_9$, $R_{10}$, $R_{11}$ and $R_{12}$ are independently selected from hydrogen, substituted or unsubstituted branched or straight chain $C_1$-$C_{10}$ alkyl, alkenyl, or alkynyl group, including without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pentyl; cycloalkyl, heterocycloalkyl, haloalkyl, benzyl, alkyl-aryl; substituted or unsubstituted aryl or heteroaryl groups; $C_1$-$C_6$ alkoxy, amino, alkyl amino, dialkyl amino, hydroxyl, hydrido, carboxy, cyano, or halogen. Preferably $R_4$ is methyl.

In one embodiment, the alkenyl-functionalized polymer will comprise one or more alkenyl-functionalized side chains. In this embodiment, any of $R_1$, $R_2$, $R_3$, $R_4$, $R_5$ and $R_6$ may independently be the fragment:

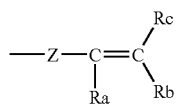

wherein Z is as defined above for $Z_1$ and $Z_2$ and $R_a$, $R_b$, and $R_c$ are independently selected from hydrogen, substituted or unsubstituted branched or straight chain $C_1$-$C_{10}$ alkyl, alkenyl, or alkynyl group, including without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pentyl; cycloalkyl, heterocycloalkyl, haloalkyl, benzyl, alkyl-aryl; substituted or unsubstituted aryl or heteroaryl groups; $C_1$-$C_6$ alkoxy, amino, alkyl amino, dialkyl amino, hydroxyl, carboxy, cyano, or halogen. Preferably $R_4$ is methyl.

"m" represents any integer greater than 2 and will typically be between about 3 and about 5,000 and is preferably selected to provide a polymer having a molecular weight of about 800 to about 550,000 g/mol. As will be evident to the skilled artisan, the viscosity of the alkenyl-functionalized organopolysiloxane can be varied by controlling the degree of polymerization and the ratio of T and Q structures. In this regard, suitable organosiloxane polymers will typically have a viscosity of about 5 up to about 20,000,000 centiStokes.

In one currently preferred embodiment of the invention, the organosiloxane polymer comprises a polydimethylsiloxane polymer (i.e., $R_5$ and $R_6$=methyl). The polydimethylsiloxane polymer has two or more alkenyl-functionalized terminal groups or side chains.

The alkenyl-functionalized organopolysiloxane may further comprise monomers having branching points of the T or Q type. When present, the T and Q structures will typically represent less than about 50%, preferably less than about 20%, and more preferably less than about 10% of the total repeat units in the cross-linked organopolysiloxane polymer. The alkenyl-functionalized organopolysiloxane polymer may be a homopolymer defined by formula I or block, alternating, or statistical copolymer comprising the polymers of formula I. The copolymer of the alkenyl-functionalized siloxane may be a grafted or blocked copolymer of silicone acrylate, silicone polyamide, silicone polyether, fluorinated silicone, silicone polyurethane, and the like.

There alkenyl-functionalized siloxane component may be a straight chain, branched, cyclic, or network structure, however, straight chain or slightly branched structures are preferred. The molecular weight of the alkenyl-functionalized siloxane component is not specifically restricted, and thus the viscosity may range from low viscosity liquids to very high viscosity gums. In order for the cured product to be obtained in the form of the rubbery elastomer, it is preferred that the viscosity at be at least 100 centistokes at 25° C.

Exemplary alkenyl-functionalized siloxanes include without limitation methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl) polysiloxanes, and dimethylvinylsiloxy-terminated dimethylsiloxane-methyl-(3,3,-trifluoropropyl) siloxane copolymers.

A second component of the cross-linking system is a hydrosilane polymer having at least two reactive Si—H bonds at either the terminal ends of the polymer or on one or more side chains. The hydrosilane polymer will typically, although not necessarily, have the structure shown in Formula II:

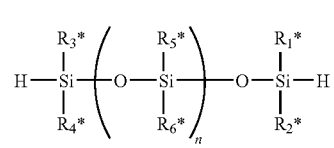

Wherein $R_1^*$, $R_2^*$, $R_3^*$, $R_4^*$, $R_5^*$, and $R_6^*$ are independently selected from substituted or unsubstituted branched or straight chain $C_1$-$C_{10}$ alkyl, alkenyl, or alkynyl group, including without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pentyl; cycloalkyl, heterocycloalkyl, haloalkyl, benzyl, alkyl-aryl; substituted or unsubstituted aryl or heteroaryl groups; $C_1$-$C_6$ alkoxy, amino, alkyl amino, dialkyl amino, hydroxyl, hydrido, carboxy, cyano, or halogen; or $R_1^*$, $R_2^*$, $R_3^*$, $R_4^*$, $R_5^*$, and $R_6^*$ may each independently represent branching points in the organopolysiloxane backbone whereby D, T, or Q structures are introduced.

In one embodiment, $R_5^*$, and $R_6^*$ are both methyl such that the polymer comprises the repeat unit of a polydimethylsiloxane (PDMS) polymer. In another embodiment, $R_1^*$, $R_2^*$, $R_3^*$, and $R_4^*$ are each methyl. In a preferred embodiment, $R_1^*$, $R_2^*$, $R_3^*$, $R_4^*$, $R_5^*$, and $R_6^*$ are each methyl.

Exemplary hydrosilanes include without limitation alkyl-trihydrosilanes, aryltrihydro-silanes, dialkyldihydrosilanes, diaryidihydrosilanes, trialkylhydrosilanes, triarylhydrosilanes, alkylhydrosiloxanes and arylhydrosiloxanes. Special mention may be made of polymethylhydrosiloxanes, t-butyldimethylhydrosilane, triethylhydrosilane, diethyldihydrosilane, triisopropylhydrosilane and mixtures thereof.

The hydrosilane will comprise at least 2 silicon-bonded hydrogen atoms in each molecule. In practice, it has been found desirable, although not strictly necessary, to provide both polymeric components such that the sum of the number of alkenyl groups in each molecule of the alkenyl-functionalized siloxane component and the number of silicon-bonded hydrogen atoms in each molecule of hydrosilane is at least 5. Where the sum of alkenyl groups and silicon-bonded hydrogen atoms, only a weak network structure is formed.

The hydrosilane component may be branched or straight chain, cyclic, or any combination thereof. The molecular weight of this component is not specifically restricted but is preferably between about 1 and about 100,000 daltons in order to obtain good miscibility with alkenyl-functionalized siloxane component. It is desirable, but not required, that this component be added in a quantity such that the molar ratio between the total quantity of silicon-bonded hydrogen atoms in the hydrosilane component and the total quantity of all lower alkenyl groups in alkenyl-functionalized siloxane component falls within the range of about 1.5:1 to about 20:1. In practice, it has been found difficult to obtain good curing properties when the molar ratio falls below about 0.5:1. At molar ratios above about 20:1 the resultant films may be undesirably hard when the cured product is heated and thus not suitable for some applications.

As an optional expedient, siloxane polymers having only one alkenyl-functionalized terminal group or side chain and/or hydrosilanes having only one Si—H unit may also be added to the film-forming compositions to impart additional control over the cross-linking density. It is within the skill in the art to determine the amounts of such optional monofunctionalized components to achieve a desired degree of cross-linking.

The catalyst may be any catalyst capable of affecting the addition reaction. Preferably, the catalyst is one which is capable of initiating the addition reaction below body temperature so as to achieve rapid cross-linking (i.e., about 5 seconds to about 5 minutes). Group VIII metal catalysts, including cobalt, platinum, ruthenium, rhodium, palladium, nickel, osmium and iridium catalysts, are contemplated to be suitable for the practice of the invention. Preferably, the catalyst is a platinum, rhodium, or palladium catalyst, and more preferably, the catalyst is a platinum catalyst, including without limitation chloroplatinic acid, platinum acetylacetonate, complexes of Pt(II) with olefins, Pt(0) complexes with phosphines, $PtO_2$, $PtCl_2$, $PtCl_3$, $Pt(CN)_3$, $PtCl_4$, $H_2PtCl_6.6H_2O$, $Na_2PtCl_4.4H_2O$, $PtCl_2$-olefin complexes, $H(PtCl3$-olefin) complexes, hexamethyldiplatinum, Pt(0)-vinylsiloxanes, Pt(0) catalysts such as Karstedt's catalyst, platinum-alcohol complexes, platinum-alkoxide complexes, platinum-ether complexes, platinum-aldehyde complexes, platinum-ketone complexes and the like. Suitable rhodium catalysts include without limitation rhodium complexes such as rhodium(III) chloride hydrate and $RhCl_3(Bu_2S)_3$. Other hydrosilylation (addition) catalysts are described in, for example, U.S. Pat. Nos. 6,307,082, 5,789,334, 4681963, 3,715,334, 3,775,452, 3,814,730, 3,159,601, 3,220,972, 3,576,027, and 3,159,662, the disclosures of which are hereby incorporated by reference.

There is essentially no constraint on the amount of catalyst that will be present in the composition. Typically, the catalyst will be present in a weight ratio to the alkenyl-functionalized organosiloxane and hydrosilane polymers of about 1:1,000 to about 1:5. It may be desirable to employ an amount of catalyst toward the higher end of this range to account for the fact that diffusion in a viscous film is limited. A preferred range is about 1:100 to about 1:10.

b. Film Forming Systems

In accordance with another aspect of the invention, film forming systems comprising the film forming compositions are provided. The film forming systems are designed to prevent the cross-linking reaction from occurring prior to application yet provide convenient means for application. The film forming systems are generally one-part systems or two-part systems.

Suitable commercially available hydrosilylation (addition) cross-linking compositions which may be readily formulated into such one or two-part systems include without limitation Dow Corning 8-8024 Base and Dow Corning 8-8024 Curing Agent, Dow Corning 7-9800 Part A&B Soft Skin Adhesive™, and Dow Corning 7-6800 Part A&B Silky Touch™, Dow Corning's Silastic® Liquid Silicone Rubber (LSR), Dow Corning C6 LSR serial, Silastic® Q7 serial, Silastic® 590 LSR Part A&B, Silastic® 591 LSR Part A&B, Silastic® LSR 9151-200P, Silastic® LSR 9451-1000P, and Silastic® 5-8601 LSR fluorosilicone materials. Similar LSR products are available from General Electric Advanced Materials under the names Silopren® LSR, LIM® LSR, LSR Topcoat, and Addisil®. Two-part Room Temperature Vulcanising (RTV) Rubbers from GE and Dow Corning under the names RTV615 and RTV627 provide additional examples of commercially available hydrosilylation (addition) cross-linking system.

i. One-Part Systems

In a one-part system, the alkenyl-functionalized organosiloxane, the hydrosilane and catalyst will necessarily be packaged together. Various methods for preventing the cross-linking reaction from occurring prior to application may be envisaged, all of which are contemplated to be within the scope of the invention. However, particular embodiments described below are consider to be currently preferred.

In one interesting implementation of the invention, the film-forming system is a one-part, multi-use system having a continuous phase comprising the alkenyl-functionalized siloxane dissolved in a carrier medium and a disperse phase comprising a plurality of microcapsules dispersed in the continuous phase. Because it is necessary to prevent the three components (alkenyl-functionalized siloxane, hydrosilane and catalyst) from coming into contact prior to use, either the hydrosilane or the catalyst may be disposed within the plurality of microcapsules. Preferably, the catalyst is contained within the microcapsules. Only when the microcapsules are ruptured or otherwise degraded do the three components come into intimate contact and thus initiate the cross-linking reaction.

As is well known in the art, encapsulating materials can be selected which will release the catalyst upon exposure to moisture, pH change, temperature change, solubility change, or mechanical shear. Suitable encapsulating materials and methods of preparing encapsulated materials, such as spray drying, extrusion, coacervation, fluidized bed coating, liposome entrapment and others, are disclosed in, for example, U.S. Pub. No. 2005/0000531 A1, Jens Uhlmann, Brigit Schleifenbaum, Heinz-Jurgen Bertram, "Flavor encapsulation technologies: an overview including recent developments" *Perfumer and Flavorist*, 27, 52-61, 2002, and "Selection of Coating and Microencapsulation Processes" by Robert E. Sparks and Irwin Jacobs in *Controlled-Release Delivery Systems for Pesticides*, Herbert B. Scher ed., Marcel Dekker, New York, N.Y., 1999, pp 3-29, the contents of which are hereby incorporated by reference. Moisture sensitive microcapsules will suffer the disadvantage of requiring anhydrous conditions prior to use and are therefore less preferred than microcapsules which release their contents by other mechanisms when employed in re-usable formulations where ambient moisture may be introduced into the packaging during use.

Preferably, an inert carrier is also present to solubilize the alkenyl-functionalized organosiloxane and provide for efficient application. There is essentially no constraint on the selection of carrier. However, the carrier should ideally be anhydrous, unreactive in the presence of the alkenyl-functionalized organosiloxane, and compatible with a cosmetic or personal care product. Suitable carriers include, for example, hydrocarbon oils, including without limitation $C_8$-$C_{20}$ hydrocarbons such as isododecane, and silicone oils including without limitation hexamethyldisiloxane (HMDS), polydimethylsiloxane (dimethicone) polymers, and cyclodimethicones. Suitable non-volatile dimethicone polymers are available from Dow Corning under the name Dow Corning 200® Fluid and have viscosities ranging from 5 to 600,000 centiStokes.

Non-polar, volatile oils particularly useful in the present invention are selected from the group consisting of silicone oils; hydrocarbons; and mixtures thereof. Such non-polar, volatile oils are disclosed, for example, in Cosmetics, Science, and Technology, Vol. 1, 27-104 edited by Balsam and Sagarin, 1972. The non-polar, volatile oils useful in the present invention may be either saturated or unsaturated, have an aliphatic character and be straight or branched chained or contain alicyclic or aromatic rings. Examples of preferred non-polar, volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals.

Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of cyclomethicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.).

Suitable non-volatile, non-polar emollients for use in the compositions of the invention are disclosed, for example, in Cosmetics, Science, and Technology, Vol. 1, 27-104 edited by Balsam and Sagarin, 1972; U.S. Pat. No. 4,202,879; and U.S. Pat. No. 4,816,261, the disclosures of which are hereby incorporated by reference. Non-volatile oils useful in the present invention are essentially non-volatile polysiloxanes, paraffinic hydrocarbon oils, and mixtures thereof. Suitable polysiloxanes useful in the present invention are selected from the group consisting of polyalkylsiloxanes, polyarylsiloxanes, polyalkylarylsiloxanes, poly-ethersiloxane copolymers, and mixtures thereof. Special mention may be made of polydimethyl siloxanes having viscosities of from about 1 to about 600,000 centistokes at 25° C., including without limitation the Viscasil series of polyalkylsiloxanes (General Electric Company) and the Dow Corning 200 series (Dow Corning Corp.). Suitable polyalkylarylsiloxanes include polymethylphenyl siloxanes having viscosities of from about 15 to about 65 centistokes at 25° C. such as, for example, those available as SF 1075 methyl-phenyl fluid (General Electric Company) and 556 Cosmetic Grade Fluid (Dow Corning Corp.). Useful polyethersiloxane copolymers include, without limitation, a polyoxyalkylene ether copolymer having a viscosity of about 1200 to 1500 centistokes at 25° C., including for example SF1066 organosilicone surfactant (General Electric Company).

The carrier will typically comprise from about 10% to about 90% by weight of the film-forming composition, and more typically between about 30% and about 80% by weight. In preferred embodiments, the carrier comprises between about 50% and about 70% by weight of the film-forming composition.

It is also contemplated that one-part systems may be formulated where all three components are present in admixture along with a hydrosilylation inhibitor which prevents the cross-linking reaction from occurring prior to the occurrence of a triggering event, such as evaporation or sublimation of the inhibitor, temperature increase, pH change, photo-activation and the like. Non-limiting examples of hydrosilylation inhibitors are described in U.S. Pat. Nos. 3,445,420, 4,256,870, 4,465,818, 4,562,096, and 5,629,387, the disclosures of which are hereby incorporated by reference. It is well within the skill in the art to select a suitable hydrosilylation inhibitor.

The one-part systems may be packaged in any conventional manner, including bottles, tubes, tubs, and the like. When so packaged the composition may be applied to the biological surfaces with any type of applicator known in the art, including sprays, swabs, brushes, towelets, and applicator tips integral with the package.

ii. Two-Part Systems

In another embodiment of the invention, the hydrosilane and the catalyst are physically separated prior to use. The system may be in the form of a first component comprising the alkenyl-functionalized organosiloxane and catalyst and a second component comprising the hydrosilane and optionally additional alkenyl-functionalized organosiloxane. Both the first and second components may further comprise a carrier material, as described above.

The first and second components may be packaged separately, for example in two containers, bottles, tubes, and the like, or may be packaged in one container having a physical partition which prevents the first and second components from coming into contact as described in, for example, U.S. Pub. No. 2004/0165935 A1 and U.S. Des. Pat. Nos. D449,224, D326,606 and U.S. Pat. Nos. 6,789,971, 6,247,586, 5,318,203, 4,196,808 and 3,757,782 the contents of which are hereby incorporated by reference.

In use, it is preferred to first apply the component comprising the alkenyl-functionalized organosiloxane and catalyst to a surface as a base coat. Thereafter, the component comprising the hydrosilane is applied as a top coat over the base coat. The base and top coats are applied onto the surface sequentially with a mixing ratio from about 1:1 to about 5:1. Alternatively, the first and second components may be mixed immediately prior to use and applied as one coating to the surface.

Alternatively, the first and second parts are separated by a dual component package, such as a dual cartridge with a mixer nozzle and applied as a single step. The skilled artisan will recognize that the foregoing embodiments are merely illustrative and all systems in which the three components are prevented from reacting prior to use are considered to be within the scope of the invention.

The first or second components may optionally comprise an agent for accelerating the hydrosilylation (addition) reaction. Such agents are well known in the art and disclosed in, for example, U.S. Pat. No. 6,303,728, the disclosure of which is hereby incorporated by reference.

c. Products

The film-forming systems may be useful in a variety of cosmetic and personal care products, including without limitation, lipsticks and lipcolors, water-proof mascaras, transfer-resistant foundations, solvent-free nail enamels, water-proof sunscreens and insect repellents, skin care products, hair care products, tooth-whitening products, antiperspirants and deodorants, and other cosmetic products.

Various fillers may be added to reinforce to film forming systems. When present, fillers may be added to the continuous phase of the one-part systems and both the first and second components of the two-part systems. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

Additional pigment/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. Other useful powders are disclosed in U.S. Pat. No. 5,688,831, the disclosure of which is hereby incorporated by reference.

Where the product is a color cosmetic, such as a lipstick, lip gloss, nail enamel, mascara, foundation, and the like, the compositions will further comprise one or more coloring agents. It is within the skill in the art to choose coloring agents and combinations of coloring agents to produce a desired color. Suitable coloring agents, including pigments, lakes, and dyes, are well known in the art and are disclosed in the C.T.F.A. Cosmetic Ingredient Handbook, First Edition, 1988, the contents or which are hereby incorporated by reference. Organic pigments include, for example, FD&C dyes, D&C dyes, including D&C Red, Nos. 2, 5, 6, 7, 10, 11, 12, 13, 30 and 34, D&C Yellow No. 5, Blue No. 1, Violet No. 2. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Other suitable colorants include ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and the like. The colorants may be surface modified with, for example, fluoropolymers, to adjust one or more characteristics of the colorant as described in, for example, U.S. Pat. Nos. 6,471,950, 5,482,547, and 4,832,944, the contents of which are hereby incorporated by reference. Suitable pearling pigments include without limitation bismuth oxychloride, guanine and titanium composite materials containing, as a titanium component, titanium dioxide, titanium lower oxides or titanium oxynitride, as disclosed in U.S. Pat. No. 5,340,569, the contents of which are hereby incorporated by reference.

In one embodiment, a long-lasting, water-proof, tack-free nail enamel is provided comprising the film-forming systems of the invention. Advantageously, all of the nitro-cellulose commonly found in nail enamels as a film-former can be replaced by the films disclosed herein. Thus, "nitro-cellulose free" nail enamels may be formulated by including the film-forming systems of the invention in place of nitro-cellulose, or other film-forming polymers, in nail formulations such as those described in U.S. Pat. Nos. 6,126,952, 5,977,217, 5,863,523, 5,607,665, 5,424,061, and 5,225,195 the disclosures of which are hereby incorporated by reference.

In another interesting embodiment, the film forming systems of the invention are formulated in lipstick and lipcolor products. Lipsticks and lipcolors may be prepared by including the film-forming systems of the invention in any formulation for such products in place of conventional film-formers. Such conventional lip products include, without limitation, U.S. Pat. Nos. 6,509,009, 6,428,797, 6,261,576, 5,747,017, 5,318,775, and 4,935,228, the disclosures of which are hereby incorporated by reference. The film-forming systems of the present invention are ideally suited for lip products because they are highly resistant to transferring color to objects which come into contact with the lips, such as glasses, cups, including Styrofoam, napkins, clothing, fingers, and the like. Further, the films of the invention are highly flexible which contributes to their long-wearing properties, decreased cracking, and increased comfort as compared to prior art lip products.

In addition to color cosmetics, the films may be incorporated into any product where it is desirable to hold a functional agent in contact with a biological surface. In addition to pigments, lakes, dyes, opacifiers, and pearling agents, the functional agent may be, for example, insect repellants, UV absorbers, UV blockers, antiperspirants, moisturizers, conditioners, tooth whiteners, and the like.

In a further embodiment, the film forming system is formulated into a tooth whitening product. The product may comprise various whitening agents, including for example, chlorine dioxide, hydrogen peroxide, calcium peroxide, metal chlorites, perborates, persulfates, peroxyacids, urea peroxide and percarbonate salts, including sodium percarbonate. Other components suitable for use in tooth whitening products include, but are not limited to those described in U.S. Pat. Nos. 6,824,704, 6,770,266, 6,514,483 and 6,290,935, the disclosures of which are hereby incorporated by reference. The films of the present invention serve to improve the benefits of such tooth whitening compositions by holding the whitening agents against the teeth in a long-lasting and water-resistant film.

The compositions of the invention may optionally comprise other active and inactive ingredients typically associated with any of the foregoing cosmetic and personal care products, including, but not limited to, excipients, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, staining agents, depigmenting agents, hypopigmenting agents, preservatives, stabilizers, pharmaceutical agents, photostabilizing agents, and mixtures thereof. In addition to the foregoing, the personal care products of the invention may contain any other compound for the treatment of skin disorders.

EXAMPLE 1

A lip gloss according to the invention is provided as a two-part formulation comprising a base coat and a top coat. The base coat comprises the cross-linkable organosiloxane polymer and other ingredients as shown in Table 1.

TABLE 1

| Lip Gloss Base Coat | |
|---|---|
| Dow Corning 8-8024 Base | 70 |
| Cyclopentasiloxane | 20 |
| Pigment Blend | 10 |

The Dow Corning 8-8024 Base comprises a polydimethylsiloxane polymer having reactive dimethylvinyl end groups and dimethyl, methylhydrogen siloxane.

The top coat, which comprises the curing agent, is kept separate from the base coat until application to the lips. Two top coat formulations (Sample 1 and Sample 2) are provided in Table 2.

TABLE 2

| Lip Gloss Top Coat | | |
|---|---|---|
| | Sample 1 | Sample 2 |
| Dow Corning 8-8024 Curing Agent | 70 | 70 |
| Dow Corning 200 ® Fluid (1,000 CST) | 30 | — |
| Dow Corning 200 ® Fluid (30,000 CST) | — | 20 |
| Dow Corning 200 ® Fluid (100,000 CST) | — | 10 |

The top coat comprises the curing agent Dow Corning 8-8024 which contains a platinum catalyst. The Dow Corning 200® Fluids employed in the top coats are linear polydimethylsiloxane (dimethicone) polymers of various degrees of polymerization. The dimethicone fluids comprise terminal trimethylsilyl, —Si(CH$_3$)$_3$, groups and are therefore unreactive in the presence of the curing agent. The three dimethicone fluids in Table 2 differ in viscosity (centistokes, "CST"), as shown in Table 2. Thus, the Sample 2 top coat will have a relatively high viscosity as compared to the Sample 1 top coat.

EXAMPLE 2

The transfer resistance of the lip gloss formulations of Example 1 was examined in comparison to the commercial lip coloring products Lipfinity™ (Procter & Gamble) and Lip Polish™ (Maybelline) using a modification of the transfer resistance testing protocol of U.S. Pat. No. 6,074,654, the disclosure of which is hereby incorporated by reference. The testing protocol is described below.

Transfer Resistance Test Method

This method may be utilized to determine the water and oil transfer resistance and adhesion properties of a cosmetic film. This test predicts the ability of a cosmetic film to resist color transfer to objects contacting the skin. Such objects include clothing, handkerchiefs or tissues, napkins and implements such as cups, glasses and table wear, and oily fingers or objects such as oily foods.

Films formed from cosmetic compositions exhibit a degree of transfer resistance directly proportional to the hardness and solvent-resistance of the film. The hardness and solvent-resistance can be expressed as a function of the blot and rub test as described below. Standard safety measure should be observed when performing this test.

Equipment:
(1) Glass plates;
(2) Collagen sausage casing such as Nippi Casing F Grade;
(3) Constant humidity chamber adjusted to 95% relative humidity;
(4) Utility Knife;
(5) Ruler;
(6) Single-sided adhesive tape;
(7) Double-sided adhesive tape;
(8) 25 micron thickness slot draw-down bar;
(9) White Styrofoam dinner plate such as Amoco Selectables™ Plastic DL® Tableware;
(10) 1.5 inch diameter circular metal punch;
(11) 1 kilogram weight;
(12) Vegetable oil;
(13) Brush-tip cosmetic applicator; and
(14) Lint-Free Wiper, such as Kimwipes® EX-L.

Procedure:
(1) Prepare a 3×4 inch sheet of collagen sausage casing by hydrating it in a 90% relative humidity chamber for at least 24 hours.
(2) Remove the collagen sheet to ambient conditions and immediately wrap tightly around the glass plate. Attach the collagen sheet to the glass using adhesive tape. The collagen surface should be flat and free of wrinkles.
(3) Allow the collagen-wrapped slide to equilibrate at ambient conditions for 24 hours.
(4) Draw down thin (1 mil), uniform films of cosmetic on the collagen. The base coat is applied first and the top coat is applied immediately thereafter.
(5) Allow the cosmetic samples on the collagen surface to sit at ambient conditions for one hour.
(6) Using a pipette, drop three drops of vegetable oil onto the right side. Using another pipet, drop three drops of water onto the left side.
(7) Separately for the oil and water sections, distribute the oil and water evenly over the film surface with cosmetic brush applicators, brushing lightly.

(8) Allow the oil and water to remain on the film undisturbed for 15 minutes.

(9) Using a lint-free wiper, carefully blot excess oil and water from the film surface. Apply as little pressure as possible during this step.

(10) Cut two disks from a clean, white Styrofoam dinner plate using a 1.5 inch diameter circular punch. The surface and edges of each disk should be smooth and even.

(11) Firmly attach with double-sided adhesive tape the disks from step (10) to the bottom surface of the 1 kg weight.

(12) Set the weight on top of the cosmetic sample applied to the collagen surface from step (5) above so that disk #1 is in contact with the oil section of the film. And disk #2 is in contact with the water section of the film. It is important to position the weight gently so that excess force beyond 1 kg is not applied.

(13) Grasping the top of the 1 kg weight, carefully rotate the disk through 360 degrees while maintaining the 1 kg force on the film. Do not lift or press the weight into the film during the rotating motion to the weight. The entire 360 degree rotation should be completed within a time interval between 3 and 5 seconds.

(14) Lift the weight straight up off the film surface and carefully remove the disk from the weight avoiding damage to the disk.

(15) Color transfer on individual discs is based on visual assessment of the discs compared to commercial products as positive and negative benchmarks. The positive control used is Lipfinity™ (base coat) while negative control used is the Lip Polish™ product.

(16) The criteria used in the "Star Grading System" for measuring the degree of transfer is explained in Table 3.

TABLE 3

Star Grading System

| Visual Assessment of Transfer | Scale |
|---|---|
| Less than Negative Control | * |
| Equal to or slight better than Negative control | ** |
| Between Negative and Positive Control | *** |
| About equal to positive control | **** |
| Better than positive control | ***** |

The results indicate that the lip gloss formulations of Example 1 exhibit superior transfer resistance to both the positive (Lipfinity™ base coat) and negative (Lip Polish™) controls. In each case noticeably less pigment had transferred to the Styrofoam disk for both formulations of Example 1 than for the control products. The results are quantified on the basis of the Star Grading System as shown below in Table 4.

TABLE 4

| Lip Gloss formulation of Example 1 | Transfer Resistance (Oil) | Transfer Resistance (Water) |
|---|---|---|
| Base Coat (Table 1) plus Top Coat (Table 2, Sample 1) | ***** | ***** |
| Base Coat (Table 1) plus Top Coat (Table 2, Sample 2) | ***** | ***** |

EXAMPLE 3

The flexibility of the lip gloss formulations of Example 1 were examined using a modification of the flexibility testing protocol described in patent U.S. Pat. No. 6,074,654, the contents of which are hereby incorporated by reference. The flexibility of a cosmetic film is an important to both the durability (long-wear) and comfort properties of a cosmetic film.

Flexibility is measured by the latex stretch test. This test predicts the ability of the color film to resist flaking or peeling types of failure after application by movement of the skin during normal activities. The flexibility latex stretch test is based on the weight-loss measurement before and after the latex stretch.

Equipment:

(1) Ansell Industrial technicians unlined gloves (12" length, 17 mil) USDA Accepted #390, Size 9;
(2) Slanted Eyeshadow Brushes from Avon Products, Inc.
(3) Analytical balance (4 decimal places); and
(4) Ruler.

Procedure:

(1) Cut a 1 inch wide band from the wrist area of the glove, avoiding the ribbing and thumb.
(2) Mark off a 1×1 inch block in the center of smooth side of the band, avoiding the embossed number.
(3) Weigh and record the weight of the latex band; hereinafter referred to as A.
(4) Determine the initial weight of the cosmetic to be applied to the band in order to produce a dried film weighing 20 mg. This is determined by dividing 20 mg by the weight percent of non-volatile material present in the cosmetic. For example, 40 mg of a cosmetic with 50% non-volatile content must be applied to the band in order to yield a 20 mg dried film.
(5) Using a clean eyeshadow brush, evenly apply the amount of cosmetic determined in step (4) over the 1×1 inch area of the band as marked in step (2).
(6) Immediately weigh and record the combined weight of the latex band and applied cosmetic. The weight of wet film with the latex band is referred to as B.
(7) Allow the sample on the latex band from step (6) to sit at ambient room conditions for one hour.
(8) Weigh and record the combined weight of the latex band A and the applied cosmetic film; hereinafter referred to as C. Subtract A from C to determine the dried film weight D (D=C−A). This weight should be 20±2 mg.
(9) Gently stretch the latex band so that the marked film length changes from 1.00 inches to 1.75 inches.
(10) Upon observing loosened film pieces on the latex band, remove the film pieces from the latex band by vigorously wiping a clean eyeshadow brush across the surface of the film: 10 times wiping in vertical direction and 10 times wiping in horizontal direction.
(11) Carefully allow the latex band to return to its approximate original shape.
(12) Record the weight of the latex band (with the remaining cosmetic); herein referred to as E.
(13) A "Star Grading System" is used based on percentage weight loss ("PWL") to grade the flexibility of the films as follows:

TABLE 5

| Weight Loss | Scale |
|---|---|
| 100-50% | * |
| 30-50% | ** |
| 15-30% | *** |
| 5-15% | **** |
| 0-5% | ***** |

The percent weight loss of the cosmetic film is calculated using the following equation:

Percent Weight Loss $(PWL) = [1-(E-A)/(C-A)] \times 100\%$

For some very flexible films, the percentage weight loss may be negligible. Therefore, in some case, due to some dust transferred from the brush, the PWL value may become negative (weight gain).

Steps (1) through (12) are repeated three times for each cosmetic formulation tested. The average of the three PWL values is determined; herein referred to as Average Percent Weight Loss ("APWL"). Low APWL values (i.e., 0-5%) correspond to flexible films having a desirable adhesive and cohesive balance of the film. The flexibility test results for the lip gloss formulations of Example 1 are quantified on the Star Grading System as shown in Table 6.

TABLE 6

| Lip Gloss formulation of Example 1 | Flexibility |
|---|---|
| Base Coat (Table 1) plus Top Coat (Table 2, Sample 1) | ***** |
| Base Coat (Table 1) plus Top Coat (Table 2, Sample 2) | ***** |

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A method for forming an elastomeric film on a body comprising:
    applying to said body, a siloxane polymer, a functional agent and a hydrosilane or a hydrosiloxane in the presence of a cross-linking catalyst; said siloxane polymer having at least two alkenyl-functionalized terminal groups or alkenyl-functionalized side chains; said hydrosiloxane having at least two Si—H units at the terminal ends;
    wherein said cross-linking catalyst induces in situ cross-linking of said siloxane polymer through the addition reaction of said hydrosilane or a hydrosiloxane to said terminal groups or side chains of said siloxane polymer to provide a highly elastomeric, water-resistant, oil-resistant and durable film thereon;
    wherein the elastomeric film contains a functional agent, said functional agent does not migrate or transfer from the elastomeric film, and said elastomeric film is a cosmetic or personal care product, wherein said hydrosilane or hydrosiloxane is selected from the group consisting of alkyltrihydrosilanes, aryltrihydrosilanes, dialkyldihydrosilanes, diaryldihydrosilanes, trialkylhydrosilanes, triarylhydrosilanes, alkylhydrosiloxanes, arylhydrosiloxanes, t-butyldimethylhydrosilane, triethylhydrosilane, diethyldihydrosilane, triisopropylhydrosilane, or combinations thereof.

2. The method of claim 1 wherein said alkenyl-functionalized terminal groups or alkenyl-functionalized side chains comprises at least one optionally substituted branched or straight chain $C_2$-$C_{10}$ alkenyl group.

3. The method of claim 2 wherein said alkenyl-functionalized terminal groups or alkenyl-functionalized side chains comprises at least one vinyl group.

4. The method of claim 1 wherein said cross-linking catalyst comprises a metal selected from the group VIII metals.

5. The method of claim 4 wherein said cross-linking catalyst comprises a metal selected from the group consisting of palladium, platinum, and rhodium.

6. A method for entrapping a functional agent within an elastomeric film disposed on a biological surface comprising:
    contacting said biological surface with said functional agent, a siloxane polymer and a hydrosilane or a hydrosiloxane, in the presence of a cross-linking catalyst; said siloxane polymer having at least two alkenyl-functionalized terminal groups or alkenyl-functionalized side chains; said hydrosiloxane having at least two Si—H units at the terminal ends:
    wherein said cross-linking catalyst induces in situ cross-linking of said siloxane polymer through the addition reaction of said hydrosilane or hydrosiloxane to said terminal groups or side chains of said siloxane polymer to provide a highly elastomeric, water-resistant, oil-resistant and durable film thereon, said film is a cosmetic or personal care product;
    thereby preventing migration or transfer of said functional agent from said biological surface, wherein said hydrosilane or hydrosiloxane is selected from the group consisting of alkyltrihydrosilanes, aryltrihydrosilanes, dialkyldihydrosilanes, diaryldihydrosilanes, trialkylhydrosilanes, triarylhydrosilanes, alkylhydrosiloxanes, arylhydrosiloxanes, t-butyldimethylhydrosilane, triethylhydrosilane, diethyldihydrosilane, triisopropylhydrosilane, or combinations thereof.

7. The method of claim 6 wherein said functional agent is selected from the group consisting of pigments, lakes, dyes, opacifiers, pearling agents, insect repellants, UV absorbers, UV blockers, antiperspirants, moisturizers, conditioners, and tooth whiteners.

8. A formulation for providing an elastomeric film on a biological surface comprising:
    (i) a first component comprising a siloxane polymer and a cross-linking catalyst; said siloxane polymer having at least two alkenyl-functionalized terminal groups or alkenyl-functionalized side chains; and
    (ii) a second component comprising a hydrosilane or a hydrosiloxane having at least two Si—H units at the terminal ends,
    wherein said first and second components are prevented from coming into intimate contact prior to use; said first component or said second component comprises a functional agent; and
    wherein said cross-linking catalyst induces in situ cross-linking of said siloxane polymer through the addition reaction of said hydrosilane or hydrosiloxane to said terminal groups or side chains of said siloxane polymer to provide a highly elastomeric, water-resistant, oil-resistant and durable film thereon, said film is a cosmetic or personal care product, wherein said hydrosilane or hydrosiloxane is selected from the group consisting of alkyltrihydrosilanes, aryltrihydrosilanes, dialkyldihydrosilanes, diaryldihydrosilanes, trialkylhydrosilanes, triarylhydrosilanes, alkylhydrosiloxanes, arylhydrosiloxanes, t-butyldimethylhydrosilane, triethylhydrosilane, diethyldihydrosilane, triisopropylhydrosilane, or combinations thereof.

9. The method of claim 1 wherein said functional agent is selected from the group consisting of pigments, lakes, dyes, opacifiers, pearling agents, insect repellants, UV absorbers, UV blockers, antiperspirants, moisturizers, conditioners, and tooth whiteners.

10. The formulation of claim 8, wherein said functional agent is selected from the group consisting of pigments, lakes, dyes, opacifiers, pearling agents, insect repellants, UV absorbers, UV blockers, antiperspirants, moisturizers, conditioners, and tooth whiteners.

* * * * *